United States Patent [19]

Ono et al.

[11] 4,388,167
[45] Jun. 14, 1983

[54] ION SELECTIVE ELECTRODE

[75] Inventors: Noriaki Ono, Akishima; Takashi Kamiyama, Tokyo, both of Japan

[73] Assignee: Olympus Optical Company Limited, Tokyo, Japan

[21] Appl. No.: 413,133

[22] Filed: Aug. 30, 1982

[30] Foreign Application Priority Data

Sep. 7, 1981 [JP] Japan .............................. 56-131899[U]

[51] Int. Cl.³ ...................... G01N 27/26; G01N 27/30
[52] U.S. Cl. ...................................... 204/420; 204/419
[58] Field of Search ............... 204/195 M; 427/58, 50, 427/51

[56] References Cited

U.S. PATENT DOCUMENTS

| | | | |
|---|---|---|---|
| 4,168,219 | 9/1979 | Hiiro et al. | 204/195 M |
| 4,236,987 | 12/1980 | Schindler et al. | 204/195 M |
| 4,256,561 | 3/1981 | Schindler et al. | 204/195 M |
| 4,269,682 | 5/1981 | Yano et al. | 204/195 M |

FOREIGN PATENT DOCUMENTS 1558553 3/1980 United Kingdom ........... 204/195 M

*Primary Examiner*—Howard S. Williams
*Assistant Examiner*—Terryence Chapman
*Attorney, Agent, or Firm*—Parkhurst & Oliff

[57] ABSTRACT

An ion selective electrode having a silicon wafer substrate secured to one end of a tube made of insulating material by an adhesive agent and an ion sensitive film applied on the outer surface of silicon wafer substrate is disclosed. In order to prevent a portion of a side edge of silicon wafer substrate from being exposed to a sample liquid to be measured, the side edge of silicon wafer substrate is tapered and the ion sensitive film is applied on the tapered side edge as well as on the outer surface of silicon wafer substrate. The tapered side edge may be simply formed by effecting an anisotropic etching for a silicon wafer.

15 Claims, 11 Drawing Figures

FIG._1
PRIOR ART
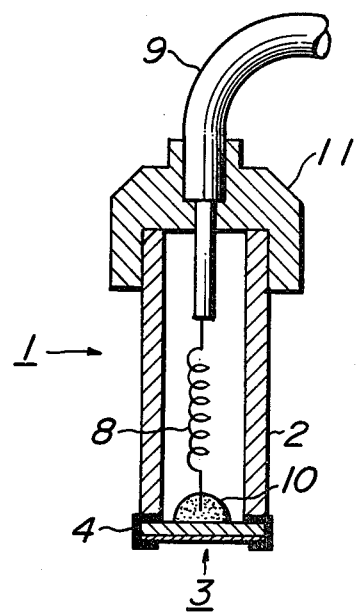
FIG._2
PRIOR ART
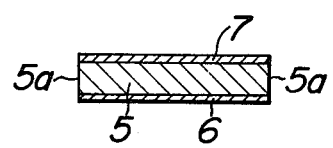
FIG._3
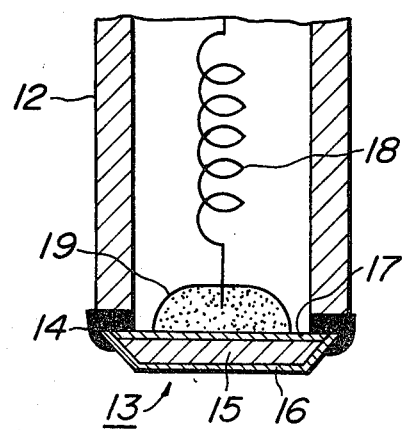

FIG._4A 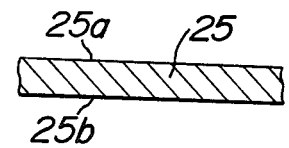
FIG._4B 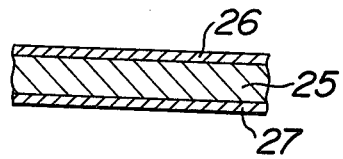
FIG._4C 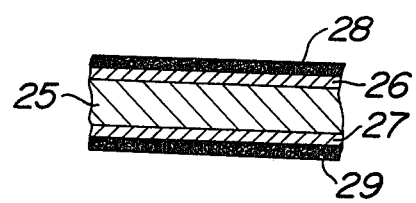
FIG._4D 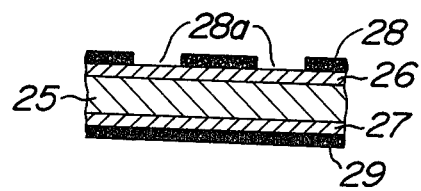
FIG._4E 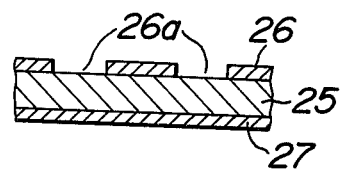
FIG._4F 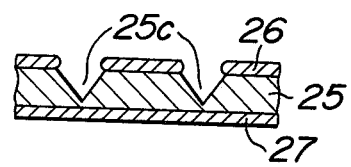
FIG._4G 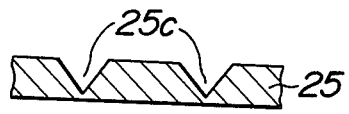
FIG._4H 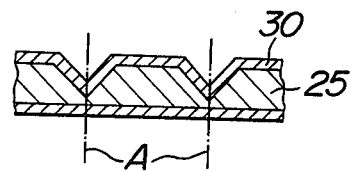

ION SELECTIVE ELECTRODE

BACKGROUND OF THE INVENTION

The present invention relates to an ion selective electrode for use in measuring a concentration of specific ion contained in a sample liquid.

Heretofore, various kinds of ion selective electrodes have been known. The inventors have also proposed an ion selective electrode comprising a tubular member made of electrically insulating material, a silicon wafer substrate applied on one end of the tubular member and an ion sensitive film applied on an outer surface of the silicon wafer substrate.

FIG. 1 is a cross sectional view showing an embodiment of such an ion selective electrode. The ion selective electrode 1 comprises a small tube 2 having a rectangular cross section and made of electrically insulating material such as plastics, and an ion sensitive body 3 applied to one end of the tube 1 by means of adhesive layer 4. As illustrated in FIG. 2, the ion sensitive body 3 comprises a silicon wafer substrate 5, an ion sensitive film 6 applied on the outer surface of the substrate 5 and an electrode film 7 formed by depositing Al and CrCu layers successively on the inner surface of the substrate 5. The ion sensitive body 3 is secured to one end of the tube 2 by the adhesive layer 4 in such a manner that the ion sensitive film 6 is exposed to the sample liquid to be measured. The adhesive layer 4 must be formed by highly insulating and waterproof material and may be formed by silicon RTV adhesive manufactured and sold by Shinetsu Silicon Co., Ltd. In order to reinforce the coupling between the tube 2 and the ion sensitive body 3, it is preferable to apply a primer onto their surfaces to be cemented. When the electrode 1 is used as a pH electrode, the ion sensitive film 6 may be constituted by a thin film of silicon nitride ($Si_3N_4$), aluminum oxide ($Al_2O_3$) or tantalum pentoxide ($Ta_2O_5$) applied on the outer surface of silicon wafer substrate 5 by means of CVD (chemical vapor deposition) or sputtering method, or may be constituted by a thin film of glass such as Corning 015 ($SiO_2$ 72.2%—$CaO$ 6.4%—$Na_2O$ 21.4%) sputtered on the silicon substrate 5. Further, when the ion selective electrode 1 is used as Na electrode, a thin film of glass of $Na_2O$ 11%—$Al_2O_3$ 18%—$SiO_2$ 68% may be sputtered on the silicon substrate 5 to form the ion sensitive film 6. To the electrode film 7 is connected a core conductor 8 of a signal wire 9 by means of solder 10, said signal wire 9 being extended via a cap 11 made of insulating material, which cap is tightly clamped onto the other end of tube 2. The core conductor 8 may be connected to the ion sensitive body 3 by means of an electrically conductive adhesive agent such as a silver paste. In such a case, the electrode film 7 may be dispensed with.

In the known ion selective electrode, since the ion sensitive film 6 is formed on the silicon substrate by CVD or sputtering method, the ion sensitive film is not or hardly formed on a side edge 5a of the silicon wafer substrate 5 and thus, the silicon wafer substrate 5 might be exposed to the sample liquid at its side edge. Therefore, in the known electrode 1 the side edge 5a of silicon wafer substrate 5 is also covered with the adhesive layer 4.

However, in practice, it is very difficult to apply the adhesive agent uniformly onto the side edge 5a of substrate. If a part of the side edge 5a of substrate 5 is exposed to the sample liquid, the sample liquid might penetrate the silicon substrate 5 and the electrode 1 might be broken in a short time. Contrary to this, if the thick adhesive layer 4 is applied, a part of the applied adhesive agent might cover a part of the ion sensitive film 6 and an effective surface area of the ion sensitive film 6 might be reduced. Then, if the size of the electrode 1 is small, an electric impedance of the electrode 1 becomes too high and thus, a response of the electrode is deteriorated and the electrode is affected extremely by noise. This limits the miniaturization of the ion selective electrode to a great extent.

SUMMARY OF THE INVENTION

The present invention has for its object to provide an ion selective electrode which can be manufactured easily and economically and can measure precisely an ion concentration during its long life time.

It is another object of the invention to provide an ion selective electrode which can be easily made small in size.

According to the invention, an ion selective electrode for measuring an ion concentration of particular ion contained in a sample liquid comprises a tubular member made of electrically insulating material;

a silicon wafer substrate applied onto one end of the tubular member and having inner and outer surfaces and a side edge at least a part of which is tapered inwardly viewed in a direction from the inner surface to the outer surface;

an ion sensitive film applied on both the outer surface and the tapered portion of side edge of silicon wafer substrate; and a signal wire having a core conductor connected to the inner surface of silicon wafer substrate and extending outwardly from the other end of tubular member.

According to the invention, the side edge of silicon wafer substrate can be advantageously tapered with the aid of an anisotropic etching.

BRIEF DESCRIPTION OF THE DRAWINGS

FIG. 1 is a cross section showing a known ion selective electrode comprising a silicon wafer substrate;

FIG. 2 is an enlarged cross section illustrating an ion sensitive body of the electrode shown in FIG. 1;

FIG. 3 is a cross section showing an embodiment of the ion selective electrode according to the invention; and FIGS. 4A to 4H are cross sections depicting an ion sensitive body at successive manufacturing steps according to the invention.

DESCRIPTION OF THE PREFERRED EMBODIMENTS

FIG. 3 is a cross section showing an embodiment of the ion selective electrode according to the invention. To one end of a tube 12 made of electrically insulating material such as plastics is secured an ion sensitive body 13 by means of an adhesive layer 14. The tube 12 has a square lateral cross section having a side of about 2.5 mm. The thickness of the tube 12 is about 0.3 mm. The ion sensitive body 13 comprises a silicon wafer substrate 15 composed of a flat square plate having a thickness of about 300 to 500 $\mu$m and an ion sensitive film 16 having a thickness of about 1,000 A and applied to the outer surface of the substrate 15 as well as to a tapered side edge of the substrate 15. In case of connecting a core conductor 18 of a signal wire to the ion sensitive body 13 by soldering, an electrode film 17 is applied on the inner surface of the silicon wafer substrate 15. The electrode film 17 is formed by depositing Al layer and CrCu layer successively. The core conductor 18 is connected to the electrode film 17 by a solder 19. The remaining construction of the ion sensitive electrode is same as that of the known electrode illustrated in FIG. 1.

The ion sensitive body 13 is secured to the one end of tube 12 by the adhesive layer 14 in such a manner that a substantial part of the ion sensitive film 16 is exposed. The side edge of the silicon wafer substrate 15 is tapered inwardly viewed in the direction from the inner surface to the outer surface and the tapered side edge is covered with the ion sensitive film 16. Therefore, the silicon wafer substrate 15 is not exposed at all to the sample liquid, even if the adhesive layer 14 covers only a part of the tapered side edge and thus, the larger area of the ion sensitive film 16 is exposed. The adhesive layer 14 may be a highly insulating and waterproof adhesive agent such as a silicon RTV adhesive agent, manufactured by Shinetsu Silicon Co., Ltd. In order to reinforce a coupling between the tube 12 and the ion sensitive body 13, a primer may be applied on surfaces of the tube 12 and ion sensitive body 13 to be bound.

It should be noted that the core conductor 18 of the signal wire may be connected to the ion sensitive body 13 by means of a conductive adhesive agent such as a silver paste. In such a case, the electrode film 17 may be omitted.

FIGS. 4A to 4H are cross sections showing successive steps of the process for forming the ion sensitive body according to the invention. The side edge of the silicon wafer substrate may be advantageously tapered by means of an anisotropic etching. At first, an N or P type silicon wafer 25 having (1, 0, 0) surfaces 25a and 25b and a thickness of about 300 to 500 μm is prepared (FIG. 4A). Then, the silicon wafer 25 is heated to a temperature of about 1,000° C. in an atmosphere of oxygen to form silicon oxide layers 26 and 27 having a thickness of about 0.5 μm on both surfaces 25a and 25b as shown in FIG. 4B. Next, on the layers 26 and 27 are uniformly applied photoresist layers 28 and 29 such as AZ13508 by means of a spinner as illustrated in FIG. 4C. Then, the photoresist layer 38 is subjected to an illumination of a given mask pattern, development and fixing to form openings 28a in the photoresist layer 28 as shown in FIG. 4D. Then, exposed portions of the silicon oxide layer 26 are etched away with the aid of an etchant formed by one part of HF and fifty parts of $H_2O$ or one part of HF and nine parts of $NH_4F$ and after that the photoresist layers 28 and 29 are removed. During this process, in the silicon oxide layer 26 there are formed openings 26a as shown in FIG. 4E. Then the silicon wafer 25 is subjected to the anisotropic etching, while the silicon oxide layers 26 and 27 are used as a mask against the etching. The etching is effected by immersing the wafer 25 into a water solution of ethylenediamine, pyrocatechol and pyrazine. When the (1, 0, 0) surface is made in contact with such an etching solution, the anisotropic etching is carried out at an angle of 54.74° and (1, 1, 1) surfaces are exposed. That is to say, V-shaped recesses 25c are formed in the silicon wafer 25 as depicted in FIG. 4F. The etching is so effected that apexes of the V-shaped recesses 25c do not reach the silicon oxide layer 27. Next, the silicon oxide layers 26 and 27 are etched away by means of the etchant of HF—$H_2O$ or HF—$NH_4F$ to form silicon wafer substrates having tapered side edges as shown in FIG. 4G. Finally, an ion sensitive film 30 is applied by sputtering on the silicon wafer substrates from the side in which the V-shaped recesses 25c have been formed as shown in FIG. 4H. In this manner, a plurality of the ion sensitive bodies are obtained by simply separating or cutting the ion sensitive bodies along lines A. It should be noted that a small part of the side edge of silicon wafer substrate thus formed is exposed, but it does not cause any problem, because the exposed part of the side edge of silicon wafer substrate is completely covered with the adhesive layer in the assembled ion selective electrode. Further, it is a matter of course that if the V-shaped recesses 25c are formed up to the silicon oxide layer 27, the side edge of silicon wafer substrate can be wholly covered with the ion sensitive film 30.

As explained above in detail, in the ion selective electrode according to the invention, since the tapered side edge of the silicon wafer substrate is covered with the ion sensitive film, the ion sensitive body can be simply secured to the tube by means of the adhesive agent and the ion selective electrode can be easily miniaturized. Further, since the silicon wafer substrate is not exposed to the sample liquid, the accurate measurement of the ion concentration can be effected for a very long life time.

Moreover, the silicon wafer generally used in the semiconductor industry is available economically. The silicon wafer is hardly affected by heat and is chemically stable. Moreover, the well established manufacturing process in the semiconductor art can be utilized in the process according to the invention and a large number of silicon wafer substrates can be manufactured at once with a high yield. Since the silicon wafer is quite cheap, the ion sensitive electrode can be made very inexpensive.

The present invention is not limited to the embodiments explained above, but may be modified in various manner. For instance, the lateral cross section of the tube is not limited to a square shape, but may be any desired shape such as circle and rectangle.

What is claimed is:

1. An ion selective electrode for measuring an ion concentration of particular ion contained in a sample liquid comprising a tubular member made of electrically insulating material;

a silicon wafer substrate applied onto one end of the tubular member by means of an adhesive layer and having inner and outer surfaces and a side edge, at least a part of which side edge is tapered inwardly viewed in a direction from the inner surface to the outer surface;

an ion sensitive film applied on both the outer surface and the tapered portion of side edge of silicon wafer substrate; and a signal wire having a core conductor connected to the inner surface of silicon wafer substrate and extending outwardly from the other end of tubular member.

2. An ion selective electrode according to claim 1, wherein the side edge of silicon wafer substrate is tapered over its whole length.

3. An ion selective electrode according to claim 1, wherein the side edge of silicon wafer substrate is tapered over only a part of its length.

4. An ion selective electrode according to any one of claims 1 to 3, further comprising an electrode film applied on the inner surface of silicon wafer substrate, whereby said core conductor of signal wire is connected to the electrode film by means of a solder.

5. An ion selective electrode according to any one of claims 1 to 3, wherein said core conductor of signal wire is connected to the inner surface of silicon wafer substrate by means of a conductive paste.

6. An ion selective electrode according to any one of claims 1 to 3, further comprising a cap made of insulating material and tightly clamped onto the other end of tubular member, whereby said signal wire is supported by said cap.

7. An ion selective electrode according to any one of claims 1 to 3, wherein said tubular member has a square lateral cross section having a side of about 2.5 mm.

8. An ion selective electrode according to any one of claims 1 to 3, wherein said silicon wafer substrate has a thickness of about 300 to 500 $\mu$m.

9. An ion selective electrode according to any one of claims 1 to 3, wherein said ion sensitive film has a thickness of about 1,000 Å.

10. An ion selective electrode according to claim 9, wherein said ion sensitive film is a chemical vapor deposited film of material selected from a group consisting of silicon nitride, aluminum oxide and tantalum pentoxide.

11. An ion selective electrode according to claim 9, wherein said ion sensitive film is a sputtered film of a material selected from a group consisting of silicon nitride, aluminum oxide, tantalum pentoxide and glass.

12. An ion selective electrode according to claim 11, wherein said glass has a composition of 72.2% $SiO_2$, 6.4% $CaO$ and 21.4% $Na_2O$.

13. An ion selective electrode according to claim 11, wherein said glass has a composition of 11% $Na_2O$, 18% $Al_2O_3$ and 68% $SiO_2$.

14. An ion selective electrode according to any one of claims 1 to 3, wherein said tapered portion of side edge of silicon wafer substrate is formed by an anisotropic etching.

15. An ion selective electrode according to claim 14, wherein said outer surface of silicon wafer substrate has a (1, 0, 0) crystal plane and said side edge of silicon wafer substrate has a (1, 1, 1) crystal plane.

* * * * *